(12) United States Patent
Dayton et al.

(10) Patent No.: US 11,992,365 B2
(45) Date of Patent: May 28, 2024

(54) DEVICES, SYSTEMS, AND METHODS FOR IMAGING WITHIN A BODY LUMEN

(71) Applicant: Boston Scientific Scimed, Inc., Maple Grove, MN (US)

(72) Inventors: Peter L. Dayton, Brookline, MA (US); Barry Weitzner, Acton, MA (US); Megan Chrobak, Groton, MA (US); Thomas Jones, Milford, MA (US); Mark W. Boden, Harrisville, RI (US); James Weldon, Newton, MA (US); Elizabeth M. Albrecht, White Bear Lake, MN (US); George Wilfred Duval, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/039,062

(22) Filed: Sep. 30, 2020

(65) Prior Publication Data

US 2021/0100528 A1   Apr. 8, 2021

Related U.S. Application Data

(60) Provisional application No. 62/911,763, filed on Oct. 7, 2019.

(51) Int. Cl.
*A61B 8/12* (2006.01)
*A61B 8/00* (2006.01)
*A61B 8/08* (2006.01)

(52) U.S. Cl.
CPC ............... *A61B 8/12* (2013.01); *A61B 8/445* (2013.01); *A61B 8/463* (2013.01); *A61B 8/5215* (2013.01); *A61B 2562/0233* (2013.01)

(58) Field of Classification Search
CPC .......... A61B 8/12; A61B 8/445; A61B 8/463; A61B 8/5215; A61B 2562/0233; A61B 1/0051; A61B 8/4494; A61B 2034/107
See application file for complete search history.

(56) References Cited

U.S. PATENT DOCUMENTS

| 8,632,461 B2 | 1/2014 | Glossop |
| 10,363,014 B1 | 7/2019 | Steinberg et al. |

(Continued)

FOREIGN PATENT DOCUMENTS

| JP | S58133228 A | 8/1983 |
| JP | H0663045 A | 3/1994 |

(Continued)

OTHER PUBLICATIONS

Komanduri, S. MD, et al. ASGE Tech Report. Gastrointestinal Endoscopy 84(2):210-221, 2016.

(Continued)

*Primary Examiner* — Sean D Mattson
*Assistant Examiner* — Michael Yiming Fang
(74) *Attorney, Agent, or Firm* — Seager, Tufte & Wickhem LLP

(57) ABSTRACT

Various embodiments are generally directed to a flexible elongate member (e.g., endoscopic accessory tool) positionable into and/or through selected anatomies, such as by generating images to position components of a flexible elongate member or to localize anatomic features, for instance. Some embodiments are directed to generating images with a plurality of imaging techniques to localize anatomic features and/or components of a flexible elongate member for one or more of inspection, orientation, and/or facilitating access to body passageways or lumens.

12 Claims, 12 Drawing Sheets

(56) References Cited

U.S. PATENT DOCUMENTS

| | | | |
|---|---|---|---|
| 2003/0176816 A1* | 9/2003 | Maguire | A61B 18/00 601/2 |
| 2004/0097789 A1* | 5/2004 | Weinberg | A61B 1/31 600/160 |
| 2006/0064009 A1* | 3/2006 | Webler | A61B 5/6852 600/434 |
| 2010/0063392 A1* | 3/2010 | Nishina | A61B 8/4488 600/439 |
| 2010/0241147 A1* | 9/2010 | Maschke | A61B 5/02007 606/159 |
| 2013/0218019 A1* | 8/2013 | Abraham | A61B 8/0841 600/466 |
| 2013/0289362 A1 | 10/2013 | Kruglick et al. | |
| 2014/0276003 A1* | 9/2014 | Wang | A61B 8/5253 600/424 |
| 2015/0094594 A1 | 4/2015 | Harhen et al. | |
| 2015/0351722 A1* | 12/2015 | Chen | A61B 8/12 600/427 |
| 2016/0335413 A1* | 11/2016 | Davidson | G16H 50/50 |
| 2018/0139392 A1* | 5/2018 | Rauniyar | A61B 1/063 |
| 2018/0214121 A1 | 8/2018 | Sliwa et al. | |
| 2019/0282210 A1* | 9/2019 | Nakatsuji | A61B 8/5207 |
| 2020/0054353 A1* | 2/2020 | Yun | A61B 17/24 606/49 |
| 2020/0330070 A1* | 10/2020 | Peterson | A61B 8/12 |

FOREIGN PATENT DOCUMENTS

| | | | | |
|---|---|---|---|---|
| JP | 2005261857 A | | 9/2005 | |
| JP | 2009018184 A | | 1/2009 | |
| KR | 101786619 B1 | * | 10/2017 | A61B 8/445 |
| WO | 2013080124 A1 | | 6/2013 | |

OTHER PUBLICATIONS

Tian, C. et al. "Cannulation time is a more accurate measure of cannulation difficulty in endoscopic retrograde cholangiopancreatography than the number of attempts" Gastroenterol Rep (Oxf). 1(3):193-197. Nov. 2013.

Tringali, A. MD, et al. "Endoscopic retrograde cholangiopancreatography: Indications, patient preparation, and complications." UpToDate. Accessed Aug. 2018. Last updated Apr. 2020.

International Search Report and Written Opinion for the International Patent Application No. PCT/US2020/053525, dated Apr. 9, 2021, 21 pages.

* cited by examiner

DEVICES, SYSTEMS, AND METHODS FOR IMAGING WITHIN A BODY LUMEN

CROSS-REFERENCE TO RELATED APPLICATION

The present application claims the benefit of priority under 35 U.S.C. § 119 to U.S. Provisional Patent Application 62/911,763, filed Oct. 7, 2019, which application is incorporated herein by reference in its entirety for all purposes.

FIELD

The present disclosure relates generally to the field of medical devices. In particular, the present disclosure relates to devices, systems and methods to facilitate entry of a flexible elongate member into and/or through selected anatomies.

BACKGROUND

Generally, performing endoscopic cannulation procedures requires advancing a guidewire and/or endoscopic accessory tool (e.g., sphincterotome, cannula, catheter, transducer, etc.) into and through patient anatomies. One example of an endoscopic cannulation procedure includes Endoscopic Retrograde Cholangio-Pancreatography (ERCP). An ERCP procedure may be used to examine the biliary duct. During an ERCP procedure, an endoscope is inserted through the mouth and advanced to the duodenum. An attempt is made to identify the common entry point for the biliary and pancreatic ducts. Once successfully identified, a guidewire may be advanced into the biliary duct to perform a variety of therapeutic procedures, such as stone management or therapy of biliary malignancies. Multiple attempts to access the biliary duct may result in a prolonged or failed procedure. In addition, tissue trauma may result from the multiple access attempts. Moreover, even if a camera is provided in the endoscope, the camera typically does not provide visualization of a duct pathway or general anatomy of the ducts beyond the common entry point. Because architecture/anatomy varies from patient to patient, lack of visualization beyond the lumen wall may require the physician to maneuver a guidewire blindly into a duct beyond the lumen wall, which may in instances result in accidental cannulation of the wrong duct.

It is with these considerations in mind that a variety of advantageous medical outcomes may be realized by the devices, systems, and methods of the present disclosure.

SUMMARY

In one aspect, the present disclosure relates to a medical device comprising a flexible elongate member having a proximal portion and a distal portion. A first transducer with a first focal region may be disposed along the distal portion of the flexible elongate member. The first transducer may be configured to generate a first image. The first image may comprise a characteristic of a wall of a body lumen. In some embodiments, the first transducer may include an optical sensor and the first image may include an optical image. The wall of the body lumen may comprise a duodenal wall. The characteristic of the wall of the body lumen may include a papilla. A second transducer may be disposed along the distal portion of the flexible elongate member. The second transducer may be configured to generate a second image. The second image may comprise a characteristic external to the wall of the body lumen. In various embodiments, the second transducer may include an ultrasonic transducer and the second image may include an ultrasound image. The characteristic external to the wall of the body lumen may include a structure behind the duodenal wall, such as a bile duct or a pancreatic duct. In some embodiments, the ultrasonic transducer is a sensor configured to detect sound waves generated by optically-excited targets and to generate an image based on the detected sound waves. In such embodiments, an energy source may be included to generate a pulse of energy to excite tissue external to the wall of the body lumen for photoacoustic imaging with the ultrasonic transducer. An articulation joint may be disposed along the distal portion of the flexible elongate member between the first transducer and the second transducer. The articulation joint may be configured to position the second transducer to facilitate generation of an image based on the first and second images. The image may include the characteristic of the wall of the body lumen and the characteristic external to the wall of the body lumen. The articulation joint may be configured to position the second transducer within at least a portion of the first focal region of the first transducer. The articulation joint may be configured to contact the wall of the body lumen with the second transducer to facilitate generation of the second image. A first balloon and a second balloon may be disposed around the distal portion of the flexible elongate member. The first and second balloons may be configured to position the first transducer or the second transducer within the body lumen. The first and second transducers may be disposed between the first balloon and the second balloon along the distal portion of the flexible elongate member. An exit of a fluid channel may be disposed between the first balloon and the second balloon to fill a region of the body lumen between the first and second balloons with a fluid to facilitate generation of the second image comprising the characteristic external to the wall of the body lumen.

In another aspect, the present disclosure relates to an apparatus comprising a processor and a memory comprising instructions that when executed by the processor cause the processor to perform one or more of the following. In some embodiments, the memory may include instructions to cause the processor to generate a first image with a first transducer. In some such embodiments, the first image may include a characteristic of a wall of a body lumen. In embodiments, the memory may include instructions to cause the processor to generate a second image with a second transducer. In many such embodiments, the second image may include a characteristic external to the wall of the body lumen. In various embodiments, the memory may include instructions to cause the processor to create a combined image comprising the characteristic of the wall of the body lumen and the characteristic external to the wall of the body lumen based on the first and second images. In one or more embodiments, the memory may include instructions to cause the processor to determine a trajectory visualization based on the first and second images. In one or more such embodiments, the memory may include instructions to cause the processor to generate an indication of the trajectory visualization in the combined image and/or an indication of the trajectory visualization with a light source inside the body lumen. The memory may include instructions to cause the processor to position the second transducer within at least a portion of a focal region of the first transducer. The memory may include instructions to cause the processor to contact the wall of the body lumen with the second transducer to facilitate generation of the second image.

In yet another aspect, the present disclosure relates to a method. The method may include generating a first image with a first transducer. The first image may include a characteristic of a wall of a body lumen. The method may include generating a second image with a second transducer. The second image may include a characteristic external to the wall of the body lumen. The method may include creating a combined image comprising the characteristic of the wall of the body lumen and the characteristic external to the wall of the body lumen based on the first image and the second image. In one or more embodiments, the method may include determining a trajectory visualization based on the first and second images. In one or more such embodiments, the method may include generating an indication of the trajectory visualization in the combined image and/or an indication of the trajectory visualization with a light source inside the body lumen. The method may include positioning the second transducer within at least a portion of a focal region of the first transducer. The method may include contacting the wall of the body lumen with the second transducer to facilitate generation of the second image. The method may include inflating one or more balloons to position the first transducer or the second transducer within the body lumen.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
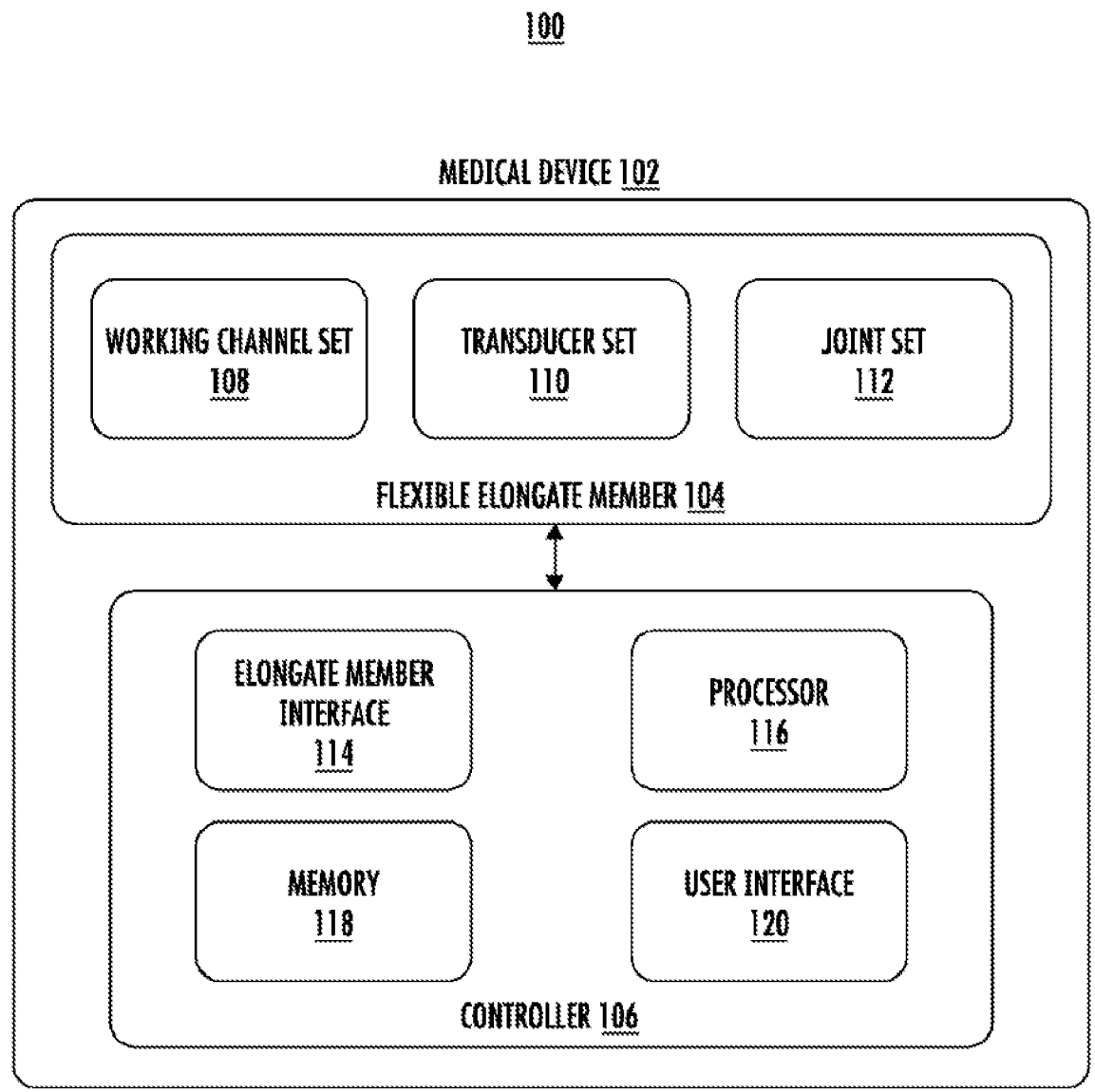
FIG. 1 illustrates an embodiment of a medical device according to the present disclosure described herein.

Various embodiments are generally directed to imaging techniques to facilitate entry of a flexible elongate member (e.g., endoscopic accessory tool) into and/or through selected anatomies, such as by generating images to position and/or to navigate components of a flexible elongate member or to localize anatomic features, for instance. Some embodiments are directed to generating images with a plurality of imaging techniques to localize anatomic features and/or components of a flexible elongate member for one or more of inspection, orientation, and/or facilitating access to body passageways or lumen, and/or navigation through body passageways/lumens.

Various additional or alternative embodiments are generally directed to imaging techniques to facilitate visualization through and beyond tissue walls, such as by generating images to position and/or to navigate to a position within a body passageway or lumen based on anatomy outside the body passageway or lumen. Some embodiments are directed to generating images with a plurality of imaging techniques to localize anatomic features and/or structures beyond the wall of the body passageway/lumen in which a flexible elongate member is navigated for one or more of inspection, orientation, and/or facilitating access to anatomical features or structures beyond the body passageway/lumen. Some embodiments are directed to coordinating such imaging techniques, with other imaging techniques, such as imaging techniques for visualizing anatomical structures and/or navigating within the body.

In one embodiment, for example, an articulation joint may be disposed along a flexible elongate member between a first transducer configured to generate a first image comprising a characteristic of a wall of a body lumen, such as a papilla of a duodenal wall, and a second transducer configured to generate a second image comprising a characteristic external to the wall of the body lumen, such as a bile duct or a pancreatic duct. In such embodiments, the articulation joint may be configured to position the second transducer to facilitate generation of a combined image comprising the characteristic of the wall of the body lumen and the characteristic external to the wall of the body lumen based on the first and second images. In embodiments, the first and second images (or the combined image) may be utilized to facilitate entry of a flexible elongate member into and/or through selected anatomies, such as a bile duct. In some embodiments, a trajectory visualization may be generated based on the first and second images. In some such embodiments, the trajectory visualization may be included in the combined image and/or generated via a light source. These and other embodiments are described and claimed.

Some challenges in facilitating entry of a flexible elongate member into and/or through selected anatomies include locating a selected anatomy and positioning a distal end of the flexible elongate member as desired to access the selected anatomy. Such challenges may result from several factors, such as the ergonomics of manipulating a multiple-degrees-of-freedom (e.g., eight) endoscope, such as a duodenoscope, into a precise location and the inability to visualize obscured or hidden entry points. For example, a target body passageway may be oriented at a difficult angle relative to an endoscopic accessory tool (e.g., obtuse angles, orthogonal, oblique), have a very small or sealed opening, or include a tortuous anatomy, blockages (e.g., stones, etc.) and benign or malignant structures. Medical professionals may make multiple attempts to achieve successful cannulation. Further, the likelihood of causing trauma to the tissues comprising or surrounding the target body passageway increases with the number of cannulation attempts. In some instances, the medical professional may be required to abort the cannulation procedure entirely.

For example, the inability to cannulate the common bile duct is one reason for a failed ERCP procedure. Adding further complexity, during the cannulation process information regarding the anatomy of the ducts beyond the common entry point may be unavailable. For instance, positional/orientation information regarding the anatomy of the ducts beyond the common entry point may be unavailable. Without information regarding the anatomy of the ducts, medical professionals attempt to maneuver a guidewire blindly into the biliary duct.

Various embodiments described herein include medical devices capable of locating a selected anatomy, positioning a flexible elongate member for access to the selected anatomy, and accessing the selected anatomy in a safe, accurate, and reliable manner. In embodiments, one or more devices described herein may utilize multimodal imaging to locate a selected anatomy, position a flexible elongate member for access to the selected anatomy, and/or access the selected anatomy. In embodiments, multimodal imaging may comprise utilizing images captured via two or more types and/or wavelengths of propagating energy. For instance, a first transducer comprising an optical sensor may be used to generate optical images within a body lumen to identify/locate characteristics of the wall of the body lumen, such as visually/optically. A second transducer comprising an ultrasonic transducer may be used to generate ultrasound images with the body lumen to identify/locate characteristics or features external to (e.g., beyond) the wall of the body lumen. A second transducer comprising a photoacoustic sensor may be used in conjunction with an energy source, calibrated to excite tissue external to the wall of the body lumen, to generate and to detect photoacoustic signals and to generate images identifying or locating characteristics or features external to (e.g., beyond) the wall of the body lumen. In such instances, information regarding selected anatomy of ducts beyond an entry point may be obtained based on the ultrasound or photoacoustic images to determine the architecture/structure of the selected anatomy. It is to be understood that the terms "transducer" and "sensor" may be used interchangeably herein without intent to indicate a difference in scope or meaning of such term. One or more selected anatomies described herein may include a patient specific anatomy. For example, in some patients, the entry point may be a common entrance to the biliary and pancreatic ducts in the duodenal wall and in other patients, the biliary and pancreatic ducts may have separate entry points in the duodenal wall.

In some embodiments, different images may be generated simultaneously and/or in real-time. In embodiments, a combined image may be generated based on a set of multimodal images. In many such embodiments, the combined image may include one or more characteristics of each image in the set of multimodal images. For example, the combined image may include the papilla in the duodenal wall from an optical image and a structure behind the duodenal wall (e.g., duct structure) from an ultrasound or photoacoustic image. In embodiments, information regarding the anatomy of the ducts (e.g., the combined image) may be displayed on a user interface, such as to communicate images and/or trajectory visualizations to a medical professional performing a cannulation procedure.

Further, in embodiments, one or more joints may be disposed at the distal end of the flexible elongate member between a distalmost tip and a more proximal region of the distal end, such as between the first and second transducers. The one or more joints may be configured to position the second transducer to facilitate generation of the combined image. For example, the one or more joints may position the second transducer such that an ultrasound image generated by the second transducer includes a characteristic external to the duodenal wall that is behind the portion of the duodenal wall captured in an optical image generated by the first transducer. In some embodiments, the one or more joints may be disposed between the first and second transducers to bring the second transducer within a focal region of the first transducer and facilitate proper positioning of the second transducer for generation of an ultrasound image. In various embodiments, articulating the second transducer via one or more joints may enable the second transducer to be placed into intimate contact with the tissue wall (e.g., duodenal wall) while allowing the first transducer to remain off the wall and continue producing useful images (e.g., optical images with identifiable characteristics).

More generally, one or more devices described herein may include one or more joints disposed along a flexible elongate member between a first location at a proximal region of the distal end of the elongate member and a second location at a distal region of the distal end of the elongate member, such as between a first transducer and a second transducer, to facilitate imaging and/or accessing a selected anatomy with the flexible elongate member. In embodiments, one or more joints may be utilized to position/orient one or more components and/or portions of the flexible elongate member, such as positioning the second transducer within a focal region of the first transducer or positioning a portion of the distal region of the flexible elongate member within a body lumen. For example, one or more of the joints may comprise inflatable balloons. In such examples, the balloons may be inflated to seal a region of a body lumen to be at least partially filled with a fluid (e.g., to facilitate ultrasonic imaging or apply a therapy). In some embodiments, one or more joints may be operated to promote cannulation, such as by vibrating, articulating, and/or actuating.

One or more of the components, devices, and/or techniques described herein may be used as part of a system to facilitate the performance of cannulation procedures in a safe, efficient, and reliable manner. In embodiments, the system according to the present disclosure may include one or more medical devices capable of locating a selected anatomy, positioning a flexible elongate member for access to the selected anatomy, and accessing the selected anatomy in a safe, accurate, and reliable manner. In these and other ways, components/techniques described here may improve patient care, increase user experience, decrease learning curve, improve success rates, and/or decrease adverse outcomes via realization of a more efficient and better functioning medical device with advantageous features. In embodiments, one or more of the components and/or features described herein may result in several technical effects and advantages over conventional computer technology, including increased capabilities and improved adaptability. For example, improved awareness of one or more selected anatomies may be provided using visualization techniques described herein. In various embodiments, one or more of the aspects, techniques, and/or components described herein may be implemented in a practical application via one or more computing devices, and thereby provide additional and useful functionality to the one or more computing devices, resulting in more capable, better functioning, and improved computing devices. Further, one or more of the aspects, techniques, and/or components described herein may be utilized to improve one or more technical fields including cannulation, diagnosis, treatment, imaging, robotics, embedded systems and/or control systems.

In embodiments, components described herein may provide specific and particular manners to enable multimodal imaging and/or cannulation. In several such embodiments, the specific and particular manners may include, for instance, controlling, monitoring, and/or interfacing with one or more of a transducer, a sensor, a joint, a working channel, and a user interface to facilitate one or more cannulation procedures. In one example, the specific and particular manner may simplify ERCP procedures to enable medical professional to quickly learn to safely and reliably access the biliary duct.

In embodiments, one or more of the components described herein may be implemented as a set of rules that improve computer-related technology by allowing a function not previously performable by a computer that enables an improved technological result to be achieved. In embodiments, the function allowed may be associated with cannulation devices and/or procedures. For example, the function allowed may include creating a combined image comprising a characteristic of a wall of a body lumen and a characteristic external to the wall of the body lumen based on the first image generated via a first imaging mode and a second image generated via a second imaging mode. In some embodiments, the function allowed may include positioning a transducer within a focal region of another transducer with one or more joints, such as to facilitate image generation with the transducer. In some embodiments, the function allowed may include generating a pulse of energy, via an energy source, to excite tissue external to the wall of the body lumen, and sensing, via a sensor, the energy generated by the tissue such as to facilitate image generation. In various embodiments, the function allowed may include utilizing one or more joints to locate and/or access objectives of a cannulation procedure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., endoscopic accessory tools and/or guidewires inserted through a duodenoscope, etc.) for selective cannulation of the common bile duct (CBD) or pancreatic duct (PD) during an Endoscopic Retrograde Cholangio-Pancreatography (ERCP) procedure, it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures and the like. The medical devices of the present disclosure are not limited to duodenoscopes, and may include a variety of medical devices for accessing body passageways or lumens, including, for example, catheters, ureteroscopes, bronchoscopes, colonoscopes, arthroscopes, cystoscopes, hysteroscopes, and the like. Further, the disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

With general reference to notations and nomenclature used herein, one or more portions of the detailed description which follows may be presented in terms of program procedures executed on a computer or network of computers. These procedural descriptions and representations are used by those skilled in the art to most effectively convey the substances of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic, or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include general purpose digital computers as selectively activated or configured by a computer program stored within that is written in accordance with the teachings herein, and/or include apparatus specially constructed for the required purpose. Various embodiments also relate to apparatus or systems for performing these operations. These apparatuses may be specially constructed for the required purpose or may include a general-purpose computer. The required structure for a variety of these machines will be apparent from the description given.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates schematically an example of an embodiment of a medical device 102 in an operating environment 100 according to the present disclosure described herein. In operating environment 100, medical device 102 may include a flexible elongate member 104 and a controller 106. The flexible elongate member 104 includes a working channel set 108, a transducer set 110, and a joint set 112. The controller 106 includes an elongate member interface 114, a processor 116, a memory 118, and a user interface 120. In one or more embodiments described herein, the components of medical device 102 may interoperate to facilitate cannulation procedures within a body lumen, such as via multimodal imaging, joint control, and/or trajectory visualizations. Embodiments are not limited in this context. It will be appreciated that the term transducer is used in a broad sense and is intended to encompass a simple sensor (input transducer), which does not generate energy signals other than to convey an image (e.g., not necessarily an actuator or output transducer), as well. Accordingly, all references herein to transducers or transducer sets should be understood to include embodiments with simple sensors and separate energy sources/energy-generating components for assisting in detecting a feature or structure.

In embodiments, controller 106 may manage, monitor, and/or operate one or more components of flexible elongate member 104. In many such embodiments, controller 106 may manage, monitor, and/or operate one or more components of flexible elongate member 104 based on execution, by processor 116, of instructions stored in memory 118. In one or more embodiments, memory 118 may include instructions to communicate information associated with, or generated by, one or more components of the flexible elongate member 104. In one or more such embodiments, memory 118 may include instructions to enable control of one or more components of the flexible elongate memory 104 based on input received via user interface 120. For example, images generated via one or more transducers in transducer set 110 may be displayed via user interface 120 and one or more joints in joint set 112 may be operated using input received via user interface 120 based on the images displayed. In some embodiments, user interface 120 may utilize augmented reality and/or virtual reality. For instance, augmented reality or virtual reality may be used to show trajectory visualizations for the flexible elongate member 104. In various embodiments, one or more components of controller 106 may be the same or similar to one or more components illustrated and described with respect to FIG. 8. In various such embodiments, controller 106 may additionally, or alternatively, include one or more components illustrated and described with respect to FIG. 8.

In some embodiments, the flexible elongate member 104 may be used as a stand-alone device for insertion into a body lumen during a cannulation procedure. However, in addition, or alternatively, embodiments the flexible elongate member 104 may be configured to extend through the working channel of another medical device (e.g., a duodenoscope, endoscope, ureteroscope, bronchoscope, colonoscope, arthroscope, cystoscope, hysteroscope, etc.). In various embodiments, flexible elongate member 104 may include a proximal portion/region and a distal portion/region. In various such embodiments, the distal region may be inserted into a body lumen. In one or more embodiments, the flexible elongate member 104 may include at least a portion of an endoscope, an endoscopic accessory tool, a tome, a cannula, a catheter, and the like. As will be described in more detail below, such as with respect to FIG. 2, in embodiments, the transducer set 110 and the joint set 112 may be disposed along the distal portion of the flexible elongate member 104.

In embodiments, the working channel set 108 may include one or more lumens that extend through at least a portion of the proximal and distal portions of the flexible elongate member 104. In several such embodiments, components may extend through one or more of the working channels to gain access to the distal portion of the flexible elongate member 104 and/or the exterior thereof. For example, a guidewire may extend through a working channel to control articulation of a joint. In another example, a wire may extend through a working channel to communicatively couple a transducer with controller 106 via elongate member interface 114. In some embodiments, working channel set 108 may include channels for internal scope operation (e.g., scope articulation) and/or scope instrument channels.

In embodiments, the transducer set 110 may include one or more sensors, transmitters, receivers, transceivers, imagers, energy sources (e.g., laser, ultrasonic, etc.), and/or lights to facilitate monitoring and/or control of the flexible elongate member 104 and/or its environment (e.g., conditions, aspects, or characteristics of a cannulation procedure). For example, transducer set 110 may include one or more of an optical sensor, a laser, an ultrasonic transceiver or probe or sensor, a distance sensor, a pressure sensor, a localization sensor, an electromagnetic sensor, a capacitive sensor, an inductive sensor, a piezoelectric sensor, fiber optics, a light, an energy source (such as for inducing a photoacoustic effect), a pH sensor, an ultraviolet sensor, an infrared sensor, a spectrometer, a temperature sensor, and the like, which can generate and/or detect signals, such as ultrasonic waves, in the body. In some embodiments, one or more portions of the flexible elongate member 104 may be disposable.

In various embodiments, the joint set 112 may include one or more connections between two bodies that allow movement. For example, joint set 112 may include one or more of a powered joint, a manual joint, an articulation joint, a telescopic joint, a balloon joint, a stabilizing joint, a pitch joint, a yaw joint, a roll joint, a vibration joint, an actuator joint, and the like. The joint set 112 may include one or more flexible portions connecting a distal tip of the flexible elongate member 104 and a proximal portion of the distal end of the flexible elongate member 104, such that the distal tip is rotatable or pivotable or otherwise positionable or movable with respect to the proximal portion. For example, the distal tip may be rotatable or pivotable about an axis substantially perpendicular to a longitudinal axis of the flexible elongate member 104. In some embodiments, the distal tip may be rotatable or pivotable along an axis non-parallel to the longitudinal axis of the flexible elongate member 104, such that the distal tip is not coaxial to the flexible elongate member. In embodiments, the distal tip may be extendable along the longitudinal axis, e.g., the flexible portion may expand or compress so the distal portion may extend distally and/or retract proximally to its relaxed position. The flexible portion may be operable manually by a medical professional, e.g., by extending a tool or other device through the working channel.

In some embodiments, the one or more flexible portions may be remotely operable via the controller and a user interface. In various embodiments, joint set 112, such as one including a plurality of flexible portions, may be automatically operated by the controller 106. In various such embodiments, the joint set 112 may be automatically operated by the controller 106 to maneuver the flexible elongate member 104 into an objective position (e.g., a target trajectory, an imaging position, a duct entry orientation, and the like). In some embodiments, the flexible elongate member 104 may have a plurality of flexible portions that can be independently expanded/compressed to maneuver/align the flexible elongate member. For example, the flexible elongate member 104 may include a plurality of longitudinal patches of independent flexible portions. In some such examples, the plurality of longitudinal patches may be disposed around the circumference of the flexible elongate member 104. In an alternative, or additional, example the flexible elongate member 104 may include a plurality of ribs that can be independently expanded and compressed.

In some embodiments, one or more aspects of the working channel set 108, the transducer set 110, and the joint set 112 may overlap. For instance, a transducer may be included in a joint or a working channel. When the transducer is included in a joint, it may measure the orientation between different ends of the joint. In another instance, a working channel may extend through and/or comprise a portion of a joint. In yet another instance, one or more of the transducer set 110 and/or the joint set 112 may be inserted through, or disposed in, one or more of working channels of working channel set 108. In embodiments, one or more articulation joints in joint set 112 may be designed to articulate one or more working channels of working channel set 108, one or more transducers of transducer set 110, and/or one or more portions of the flexible elongate member 104. In several such embodiments, the one or more articulation joints may be biased/asymmetrical to more accurately position the one or more working channels and/or one or more transducers. For instance, biased joints may return to a predetermined angle (e.g., 180 degrees) in the absence of external forces. In another instance, asymmetrical joints may implement a mechanical advantage.

In embodiments, the medical device 102 may provide guidance prior to and/or during cannulation of a body lumen, such as the duodenal or biliary duct. In one or more embodiments, the medical device 102 may include enhanced ultrasound capabilities to improve ultrasound guided cannulation. In various embodiments, ultrasound may be integrated with tools in one or more working channels or integrated into the design of a scope (e.g., a duodenoscope). In embodiments, the medical device 102 may enable both optical and ultrasound images to be captured simultaneously. The optical and ultrasound images may be fused together to create an image of both the papillae and the anatomy behind the duodenal wall. In various embodiments, an operator may be able to toggle between views, view simultaneously (if a camera and photoacoustic imaging are used, then time multiplexed with the illumination pulsing for photoacoustic imaging and steady state for direct visualization), or overlay/fuse different images together, or combinations thereof, such as via user interface 120. In some embodiments, in addition to or instead of ultrasound capabilities, the medical device 102 may include enhanced photoacoustic capabilities to improve photoacoustic guided cannulation. In some instances, photoacoustic imaging may allow differentiation of tissue or structure (e.g., differentiation between the bile duct and the pancreatic duct) better than or perhaps not even achievable by standard ultrasonic imaging. In various embodiments, photoacoustic capabilities may be integrated with tools in one or more working channels or integrated into the design of a scope (e.g., a duodenoscope). In embodiments, the medical device 102 may enable both optical and photoacoustic images to be captured simultaneously. The optical and photoacoustic images may be fused together to create an image of both the papillae and the anatomy behind the duodenal wall. In various embodiments, an operator may be able to toggle between optical and photoacoustic views, view optical and photoacoustic images simultaneously, or overlay/fuse different images together, or combinations thereof, such as via user interface 120.

In some embodiments, intraoperative guidance using ultrasound during ERCP procedures can improve duct cannulation. The ability to see the papilla with direct visualization while also being able to see (e.g., via ultrasound) the ducts behind the duodenal wall can better guide a medical professional for scope and/or tool alignment. Improving the ease of cannulation procedures, such as the duct cannulation and navigation to the target location in the biliary duct, can decrease procedural time and increase a medical professional's proficiency in performing the procedure. This may also reduce the number of inadvertent pancreatic duct cannulations and, as a result, lower pancreatitis rates.

In one or more embodiments, medical device 102 may provide a medical professional with a view of the bile and pancreatic ducts behind the duodenal wall (in the case or ERCP) or where to puncture the wall to access a duct. In some embodiments, an ultrasound transducer (see e.g., FIG. 2) may be integrated into the tip of the flexible elongate member 104 to make contact with the wall of a body lumen (e.g., tissue near the papilla) for generating an ultrasound image (see e.g., FIG. 4A). It will be appreciated that the ultrasound transducer may be a photoacoustic sensor or probe (which may be considered simpler than a standard ultrasonic transducer, yet capable of higher resolution image generation), the terms "ultrasound transducer" and "transducer" being understood herein as including such photoacoustic sensor or probe as an alternative to a standard ultrasound transducer. The photoacoustic sensor or probe may be used to detect sound waves generated by optically-excited targets beyond the tissue wall, and to generate a high resolution/high contrast ultrasound image of the optically-excited targets. In such embodiments, an energy source, such as a light source (e.g., LED, fiber optic, laser, etc.), is provided to generate the appropriate energy pulse (e.g., 100V or more) with sufficient energy to excite the target tissue (e.g., beyond a tissue wall at which transducer 210-2 is located) to generate a return pulse or echo (e.g., in a multiple of 10 mV range, and in the ultrasonic frequency range, such as in a multiple of 10 MHz range). The energy source may be the same light source used by the first transducer (e.g., light for a camera or other scope) or a separate laser or other energy source capable of generating the appropriate energy pulse. Light within the full spectrum may be used. In some embodiments, light with red wavelengths is used. The energy source is positioned along distal portion 204-2 of flexible elongate member 204 at a location selected to generate and propagate to the target site sufficient energy to excite tissue at the target site. In some embodiments, an energy source is used in conjunction with first transducer 210-1 (e.g., a light source, such as an LED or fiber optic or laser, for illuminating the pathway viewed by a camera or the like), and may serve the dual purpose of illuminating for first transducer 210-1 and generating excitation-energy (e.g., pulsed energy such as pulsed light) for a second transducer 210-2 in the form of a photoacoustic sensor. The sensor (e.g., receive-only-transducer) for photoacoustic imaging may have more refined receiver circuitry than a standard ultrasonic transducer to receive and process the finer signals (compared with standard ultrasound signals) being received, and to generate images with finer resolution and enhanced and higher contrast than may typically be achieved with standard ultrasound imaging.

In some such embodiments, one or more joints may be operated to cause the ultrasound transducer to make contact with tissue near the papilla. In other embodiments, a portion of a body lumen may be filled with a fluid to enable generation of an ultrasound image without contacting the wall of the body lumen (see e.g., FIG. 5).

In various embodiments, a set (e.g., working channel set 108, transducer set 110, joint set 112) may refer to one or more components, or combinations thereof, with common characteristics. For example, the working channel set 108 may include one or more working channels extending through at least a portion of flexible elongate member 104. In another example, the transducer set 110 may include one or more sensors used to measure and/or sense aspects of the medical device 102 and/or the environment of medical device 102. In yet another example, the joint set 112 may refer to one or more joints and/or joint mechanisms that facilitate positioning/maneuvering of the flexible elongate member 104.

Figure 2:
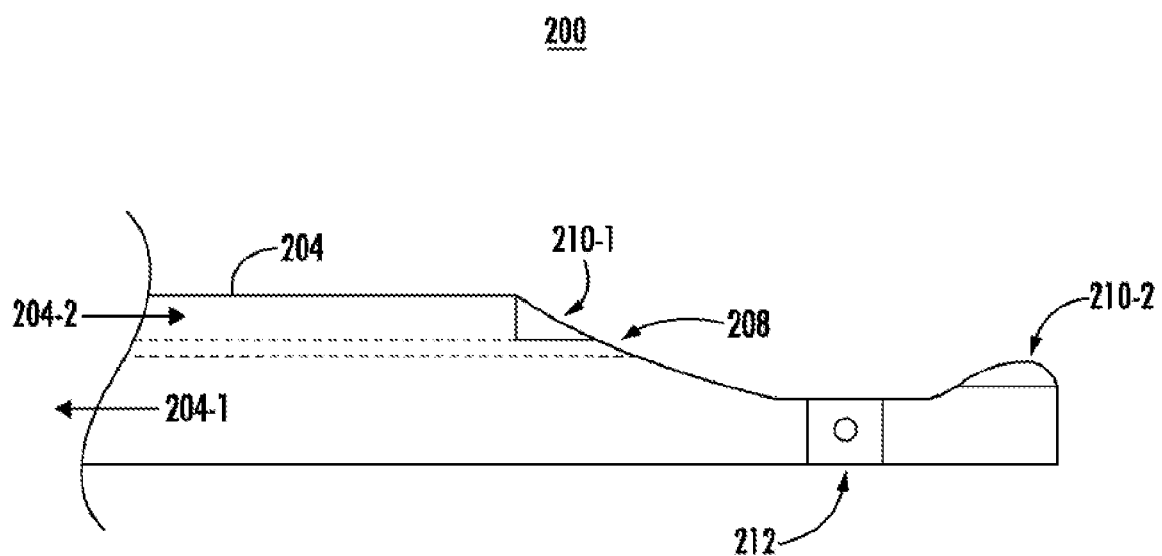
FIG. 2 illustrates an embodiment of a distal end of a flexible elongate member according to the present disclosure described herein.

FIG. 2 illustrates an example of a flexible elongate member 204 in environment 200 according to the present disclosure described herein. In some embodiments, environment 200 may include one or more components that are the same or similar to one or more other components described herein. For example, a distal end of flexible elongate member 204 may be the same or similar to distal end of the flexible elongate member 104. In environment 200, flexible elongate member 204 may include a proximal portion 204-1 and a distal portion 204-2 and a working channel 208 extending through at least a portion of the proximal and distal portions 204-1, 204-2. In the illustrated embodiments, the distal portion 204-2 of the flexible elongate member 204 includes transducers 210-1, 210-2 and articulation joint 212. The distal portion 204-2 may be considered to encompass the "distal end" of the flexible elongate member 204 with a proximal region in which the transducer 210-1 is generally located and a distal region in which the transducer 210-2 is generally located, with a distalmost-end at a generally free end of the flexible elongate member 204. In one or more embodiments described herein, articulation joint 212 may be utilized to move transducer 210-2 while keeping transducer 210-1 stationary. In some embodiments, articulation joint 212 facilitates movement of the distal region relative to the proximal region of distal portion 204-2. Embodiments are not limited in this context.

In some embodiments, articulation joint 212 may be used to position transducer 210-2 in contact with the wall of a body lumen. In various embodiments, articulation joint 212 may be used to position transducer 210-2 within a focal region of transducer 210-1. In embodiments, articulation joint 212 may be manipulated to facilitate access of the flexible elongate member 204 into a target body lumen. In various embodiments, one or more joints (e.g., joint 212) may include one or more features to facilitate operation of a scope elevator. In many embodiments, joints/working channels disposed therethrough may include one or more of a lumen, a bearing, a channel, a pivot point, a tensioner, and the like to facilitate operation of one or more components of a medical device or system.

In one or more embodiments, flexible elongate member 204 may illustrate an approach that allows multimodal imaging. For example, transducer 210-1 may comprise an optical sensor and transducer 210-2 may comprise an ultrasound or photoacoustic transducer. In such examples, transducer 210-1 may generate optical images in unison with the generation of ultrasound images by transducer 210-2. Transducer 210-1 may be an imaging device similar to an imaging device in a standard duodenoscope. In some embodiments, articulation joint 212 may be utilized in conjunction with optical images generated by transducer 210-1 to position transducer 210-2 to generate ultrasound images. In some such embodiments, transducer 210-2 may be positioned against the wall of a body lumen, such as the duodenal wall proximate the papilla.

In embodiments, articulation joint 212 may be disposed more proximate the distalmost-end of flexible elongate member 204 than transducer 210-1 and/or working channel 208. In various embodiments, the transducer 210-2 may be disposed more proximate distalmost-end of the distal end of flexible elongate member 204 than working channel 208, transducer 210-1, and/or articulation joint 212. In various embodiments, arrangement of one or more of the working channel 208, transducers 210, and articulation joint 212 may be configured to position transducer 210-1 to generate an image of a characteristic of a wall of a body lumen at the same time as positioning transducer 210-2 to generate an image of a characteristic external to the wall of the body lumen. In some such embodiments, this may facilitate positioning of the transducer 210-2 within a focal region of transducer 210-1. In embodiments, the net articulation of transducer 210-2 with respect to articulation joint 212 may be larger than the net articulation of transducer 210-1 (e.g., when articulation joint 212 is an asymmetrical articulation joint). In several such embodiments, this may facilitate positioning transducer 210-2 in contact with the wall of a body lumen (e.g., to acoustically couple the transducer/sensor to the tissue region of interest) while maintaining transducer 210-1 at a distance from the wall that allows for an imaging mode of transducer 210-1.

In some embodiments, one or more of transducers 210-1, 201-2 may comprise multiple transducers. For example, transducer 210-1 may be capable of visible and infrared imaging. In one or more embodiments, the transducer 210-1 and working channel 208 may be positioned in a manner facilitating intuitive use, such as by positioning transducer 210-1 and working channel 208 in a manner familiar with devices used in training and/or common cannulation procedures. In several embodiments, additional articulation joints may be disposed along the flexible elongate member 204. In several such embodiments, the additional articulation joints may be configured to position, at least in part, each respective transducer disposed distally of a respective articulation joint.

Figure 3:
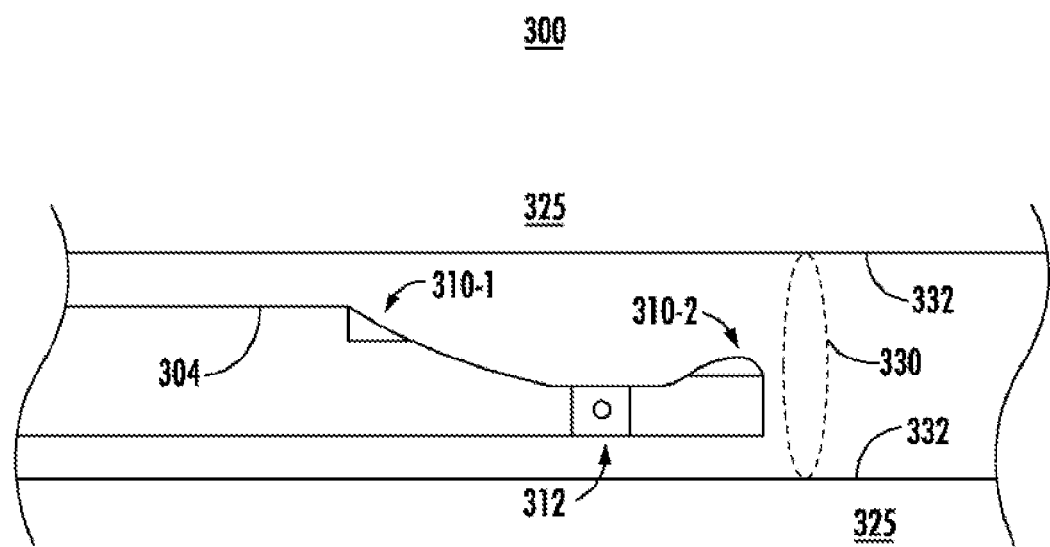
FIG. 3 illustrates an operating environment for a flexible elongate member according to the present disclosure described herein.

FIG. 3 illustrates one example of an operating environment 300 for flexible elongate member 304 according to the present disclosure described herein. In some embodiments, environment 300 may include one or more components that are the same or similar to one or more other components described herein. For example, a distal end of flexible elongate member 304 may be the same or similar to flexible elongate member 204. In environment 300, the distal end of flexible elongate member 304 may be disposed within a body lumen 330 with wall 332. Additionally, environment 300 may include external region 325 outside of the body lumen 330. In the illustrated embodiments, flexible elongate member 304 may include an articulation joint 312 disposed between a first sensor 310-1 and a second transducer 310-2. A first sensor 310-1 may be an optical sensor, and a second sensor 310-2 may be an ultrasonic transducer or sensor, although first and second sensors 310-1, 310-2 may be other sensors as described herein to facilitate an ERCP procedure. In one or more embodiments described herein, articulation joint 312 may be utilized to position ultrasonic transducer 310-2 in contact with the wall 332 for imaging. For example, the distal tip of the flexible elongate member 304 may be rotatable, pivotable, positionable, or otherwise movable out of alignment with the longitudinal axis of the flexible elongate member 304. In embodiments, ultrasonic transducer 310-2 may generate an image of a structure in the external region 325. Embodiments are not limited in this context.

In some embodiments, the positioning of one or more joints in joint set 112 may enable positioning of ultrasonic transducer 310-2 in contact with the wall 332 of body lumen 330 while allowing optical sensor 310-1 to maintain a minimum distance from the wall of the body lumen to enable effective imaging (e.g., of the visual progress of flexible elongate member 204 within the body lumen). In some embodiments, articulation joint 312 may include an articulating and telescoping joint. In many embodiments, the flexible elongate member 304 may include one or more working channels, however, working channels are not illustrated in environment 300 for simplicity. For example, flexible elongate member 304 may include a working channel that is the same or similar to the working channel 208 of FIG. 2. In one or more embodiments, articulation joint 312 may comprise an elevator to angulate the flexible elongate member 304 for access. In many such embodiments, the elevator may connect (e.g., a distal end thereof) to the flexible elongate member 304 distal of the transducer 312. In some embodiments, an elevator may be placed/connected proximate the exit of the working channel. In various embodiments, a medical device may include a plurality of elevators. In various such embodiments, one or more working channels may be utilized for operation of the plurality of elevators.

Embodiments may include different configurations of the components of flexible elongate member 304, such as distances between two or more of articulation joint 312, optical sensor 310-1, and ultrasonic transducer 310-2. In some embodiments, the distance of the ultrasonic transducer 310-2 to the articulation joint 312 may be variable. For instance, the ultrasonic transducer 310-2 and articulation joint 312 may be movable with respect to the optical sensor 310-1. In such embodiments, articulation joint 312 may extend longitudinally with respect to the flexible elongate member 304. One or more embodiments may include two or more independent articulation joints. In such embodiments, each of the two or more independent articulation joints may be disposed along the length of the flexible elongate member 304 proximal, between, and/or distal to one or more other components of the flexible elongate member 304. For example, a flexible elongate member may include one articulation joint distal to a working channel. In such example, the operator may utilize the articulation joint to adjust the working channel position by an amount of angulation of the ultrasonic transducer 310-2 against the wall 332 of body lumen 330.

Figure 4A:
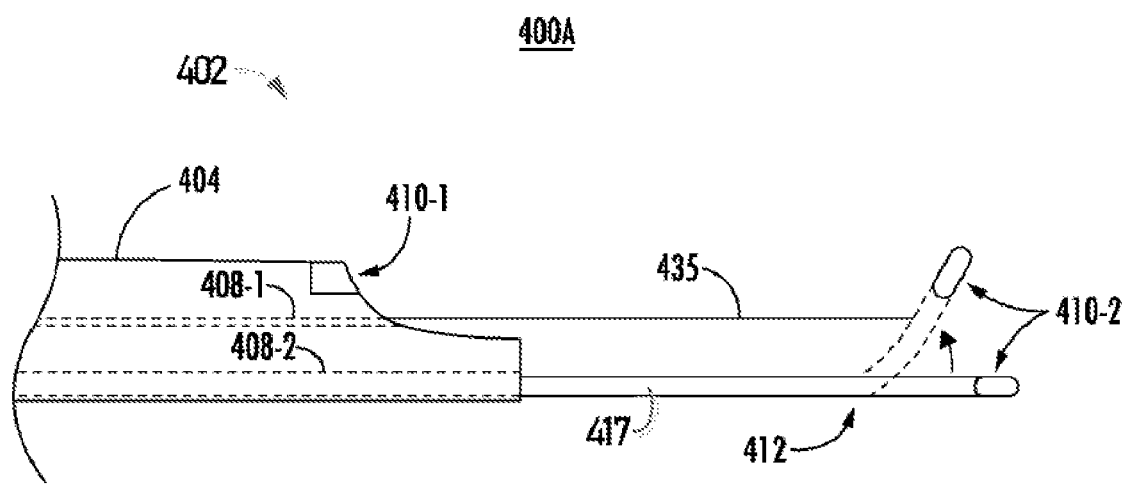
FIGS. 4A and 4B illustrate an embodiment of positioning a transducer within a focal region according to the present disclosure described herein.
Figure 4B:
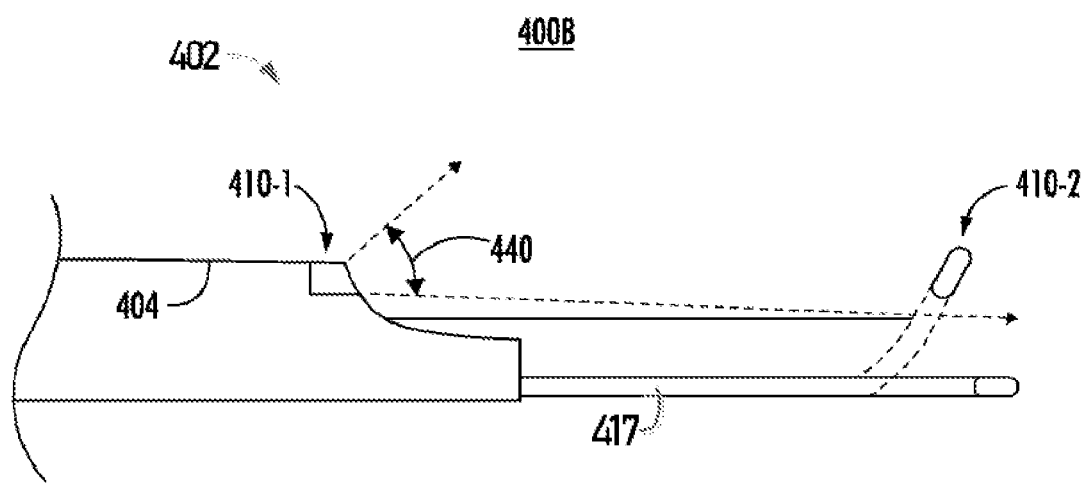

FIGS. 4A and 4B illustrate an example of an embodiment facilitating positioning a transducer within a selected focal region in environments 400A, 400B, according to the present disclosure described herein. In some embodiments, environments 400A, 400B may include one or more components that are the same or similar to one or more other components described herein. For example, optical sensor 410-1 and ultrasonic transducer or sensor (used interchangeably herein without intent to limit, a noted above) 410-2 may be included in transducer set 110. Environment 400A includes distal end of medical device 402 with flexible elongate member 404 comprising working channels 408-1, 408-2, optical sensor 410-1, ultrasonic transducer 410-2 extending though working channel 408-2, articulation joint 412, transducer member 417, and tensioner 435 extending through working channel 408-1. Environment 400B includes flexible elongate member 404 comprising optical sensor 410-1 with focal region 440 and ultrasonic transducer 410-2. In one or more embodiments, tensioner 435 may operate articulation joint 412 to properly position ultrasonic transducer 410-2, such as to overlap the focal region 440 of optical sensor 410-1 with a focal region of the ultrasonic transducer 410-2. Embodiments are not limited in this context.

In several embodiments, the distal end of tensioner 435 may be coupled to transducer member 417. In several such embodiments, the distal end of tensioner 435 may be coupled between at least a portion of the articulation joint 412 and at least a portion of the ultrasonic transducer 410-2. In some embodiments, tensioner 435 may include an elevator. In various embodiments, articulation joint 412 may include a flexible portion of a component of the medical device. For example, ultrasonic transducer 410-2 may be included in a catheter, such as an ultrasound catheter, inserted through working channel 408-2 of flexible elongate member 404. In many embodiments, flexible elongate member 404 may include, or be used in conjunction with, an endoscope. In some embodiments optical sensor 410-1 is provided on the main body (e.g., endoscope, duodenoscope, etc.) of flexible elongate member 404, and ultrasonic transducer 410-2 is provided on a separate, smaller flexible elongate member (e.g., an endoscopic ultrasound catheter) passed through a working channel of the flexible elongate member 404. In one or more embodiments, the tensioner 435 may be selectively attached to the transducer member 417. It will be appreciated that provision of ultrasonic transducer 410-2 on a separate flexible elongate member from the main flexible elongate member on which first transducer 410-1 is provided may allow for increased mobility and enhanced positionability of ultrasonic transducer 410-2 to optimize positioning thereof relative to the target tissue and consequent improved signal receipt/transmission and improved contrast for visualization, as well as potentially simplified manufacture and accompanying cost reductions.

In one or more embodiments, medical device 402 may include additional articulation joints, which, in some embodiments are independent of one another. For example, an articulation joint may be configured to extend/retract the transducer member 417. In some such examples, the articulation joint may be disposed in working channel 408-2. In an alternative, or additional, example, an articulation joint may be configuration to extend/retract the tensioner 435. In some such examples, the articulation joint may be disposed in working channel 408-1. In many embodiments, one or more characteristics of the medical device may be selected to properly position different components of the medical device 404 with respect to each other. For instance, a distance from transducer 410-2 and transducer 410-2 may be chosen based at least in part on the flexibility of articulation joint 412 and/or the transducer member 417. In some embodiments, articulation joint 412 may comprise a portion of transducer member 417 with more flexibility than one or more other portions of transducer member 417. In some embodiments, articulation is designed to articulate working channel 408-1, transducer 410-2, or both. In some embodiments in which both working channel 408-1 and transducer 410-2 are articulated, the articulation joint could be biased/asymmetrical to optimize the positions of (including relative positions of) working channel 408-1 and transducer 410-2.

In some embodiments, flexible elongate member 404 may comprise one or more portions of a two channel ERCP scope with a straight through lumen for use with an ultrasound catheter comprising ultrasonic transducer 410-2 and/or a side exiting channel with an elevator to control tool direction. In some embodiments, use of an ultrasound catheter may enable flexible elongate member 404 to be disposable. In such embodiments, the ultrasound catheter may additionally, or alternatively, be disposable. In one or more embodiments, flexible elongate member 404 may comprise one or more portions of a duodenoscope. In various embodiments, the use of a catheter ultrasound sensor may allow variable distances between the optical sensor 410-1 and the ultrasonic transducer 410-2. In one or more embodiments, the ultrasonic transducer 410-2 may have a single axis of articulation (like a sphincterotome) to facilitate making desired contact with the duodenal wall. In some embodiments, the ultrasonic probe could be a modified SpyScope© Access and Delivery Catheter such as used in the SpyGlass© Direct Visualization system sold by Boston Scientific Corporation, retrofitted for photoacoustic imaging. In the illustrated embodiment of FIG. 4B, the working channels 408-1, 408-2 are not shown for simplicity.

Figure 5:
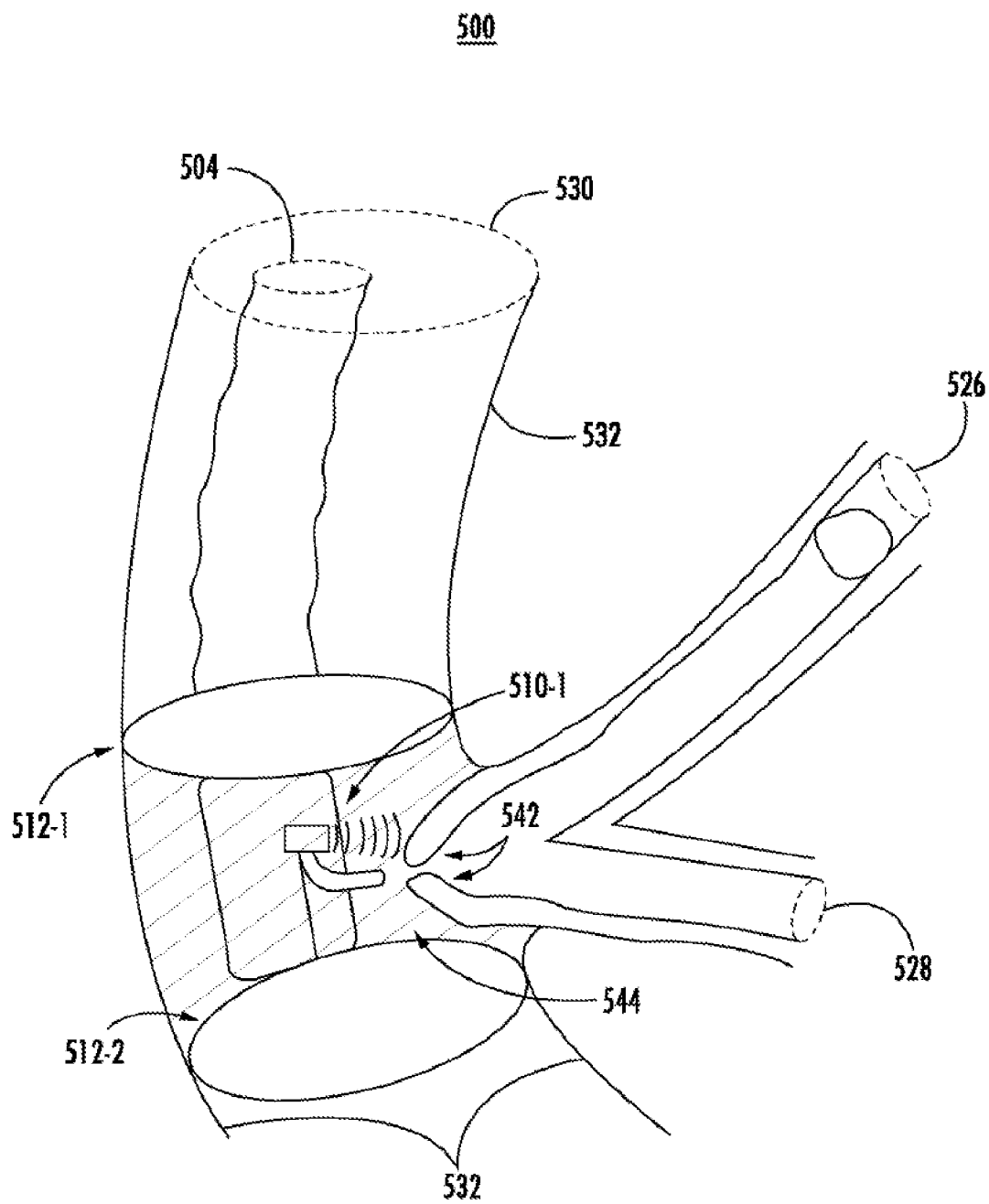
FIG. 5 illustrates an embodiment of a distal end of a flexible elongate member in an exemplary operating environment according to the present disclosure described herein.

FIG. 5 illustrates one example of an embodiment of a distal end of a flexible elongate member 504 in an operating environment 500 according to the present disclosure described herein. Although flexible elongate member 504 is disposed within duodenum 530 in environment 500, it will be appreciated that flexible elongate member 504 may be utilized in other environments without departing from the scope of this disclosure. In some embodiments, environment 500 may include one or more components that are the same or similar to one or more other components described herein. For example, balloons 512-1, 512-2 may be included in joint set 112. Environment 500 may include a duodenum 530 with a duodenal wall 532 and a flexible elongate member 504 disposed therein. Further, a papilla 542 is illustrated as a characteristic of the duodenal wall 532 and the papilla 542 comprises a common entry point to a biliary duct 526 and a pancreatic duct 528. In the illustrated embodiments, distal end of flexible elongate member 504 includes ultrasonic transducer 510-1 and balloons 512-1, 512-2. Embodiments are not limited in this context.

In one or more embodiments, the balloons 512-1, 512-2 (or balloons 512) may be operated to generate a sealed region within duodenum 530 to create fluid filled region 544. In one or more such embodiments, the fluid filled region 544 may enable ultrasonic transducer 510-1 to generate an image of a structure external to the duodenum 530, such as the structure of the biliary duct 526 and/or the pancreatic duct 528. In various embodiments, the balloons 512 may be independently operated. In several embodiments, each of the balloons may comprise an articulation joint. In some embodiments, generating an image with the ultrasound transducer 510-1 by inflating/deflating balloons 512 to avoid contacting the papilla 542 and/or duodenal wall 532 may result in reduced risk of causing irritation or inflammation.

In various embodiments, the flexible elongate member 504 may include one or more lumens (e.g., working channels) for inflating/deflating the balloons 512. For example, fluid may be added and removed from a balloon via one or more of the lumens. In many embodiments, at least one lumen may enable fluid to be added or removed from the fluid filled region 544. In some embodiments, the balloons 512 and fluid filled region 544 may be filled with different fluids. In several embodiments, the flexible elongate member may comprise a fluid channel with an exit disposed between the first balloon and the second balloon to fill a region of the body lumen between the first and second balloons with a fluid to facilitate generation of the second image comprising the characteristic external to the wall of the body lumen.

Figure 6C:
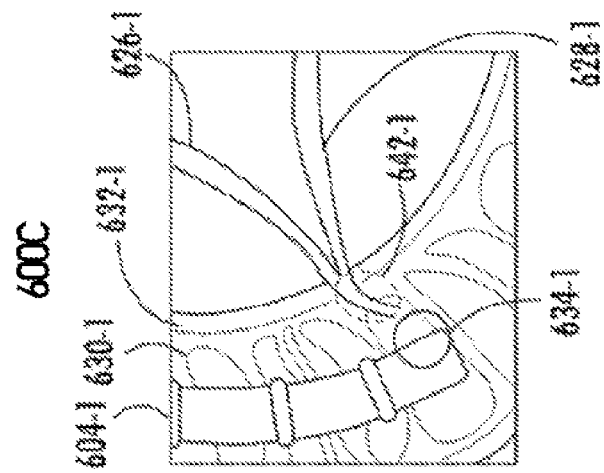
FIGS. 6A-6F illustrate embodiments of imaging and trajectory visualizations according to the present disclosure described herein.
Figure 6B:
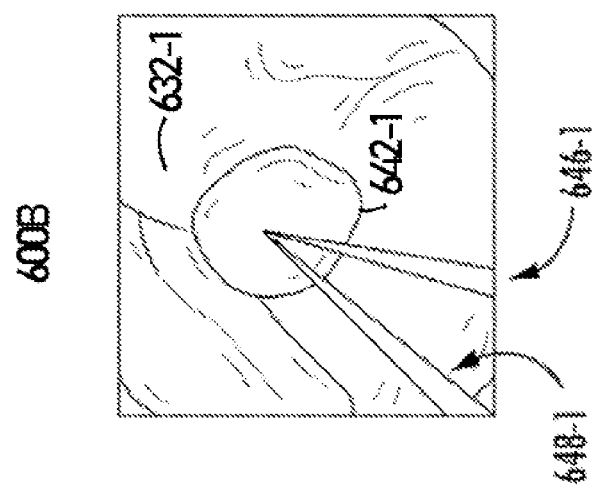
Figure 6A:
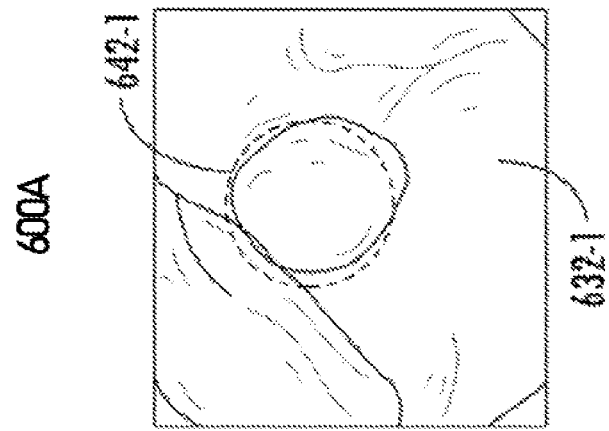
Figure 6F:
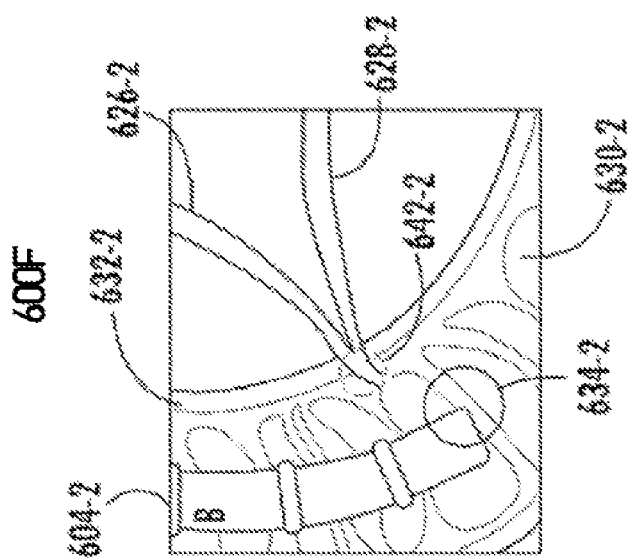
Figure 6E:
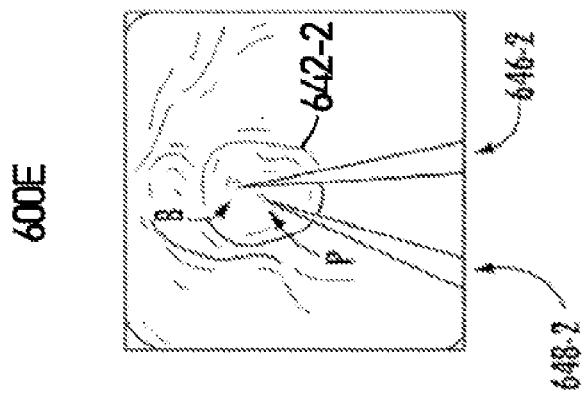
Figure 6D:
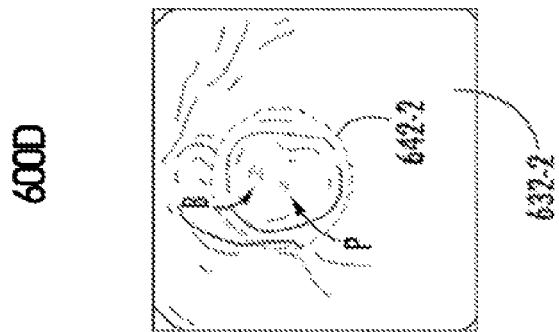

FIGS. 6A-6F illustrate embodiments of imaging and trajectory visualizations in environments 600A-F according to the present disclosure described herein. Although flexible elongate members 604 are disposed within duodenums 630, respectively, in FIGS. 6A-6F, it will be appreciated that flexible elongate member 604 may be utilized in other environments without departing from the scope of this disclosure. FIGS. 6C and 6F illustrate a distal end of a medical device such as flexible elongate member (e.g., a duodenoscope) positionable in a patient's anatomy for performing an ERCP procedure. FIGS. 6A-6B and 6D-6E illustrate images projected from an imaging device 6XX on the flexible elongate member and displayed on a user interface for a medical professional to cannulate the papilla. It is understood that flexible elongate members 604-1, 604-2 may be the same or similar to one or more of flexible elongate members 104, 204, 304, 404, 504. Environments 600A-600F illustrate different selected anatomies. Environments 600A-600C include flexible elongate member 604-1, duodenum 630-1, duodenal wall 632-1, papilla 642-1, biliary duct 626-1, pancreatic duct 628-1, light source 634-1, target trajectory visualization 646-1, and actual trajectory visualization 648-1. Environments 600D-600F include flexible elongate member 604-2, duodenum 630-2, duodenal wall 632-2, papilla 642-2, biliary duct 626-2, pancreatic duct 628-2, light source 634-2, biliary duct trajectory visualization 646-2, and pancreatic duct trajectory visualization 648-2. Embodiments are not limited in this context.

In one or more embodiments described herein, one or more features, components, and/or techniques described with respect to FIGS. 6A-6E, such as imaging-related processes may be implemented via controller 106. In embodiments, these features, components, and/or techniques may include one or more of the following. Visual feedback from a camera may be used to automate and/or guide the flexible elongate member 604-1, 604-2 to provide improved imaging (e.g., multimodal imaging). More generally, any techniques or components described herein may be used to automate and/or guide operation of one or more other components. One or more transducers, such as an ultrasound sensor, may be integrated into the flexible elongate member 604-1, 604-2. An ultrasound sensor may be used to provide acoustic radiation force impulse elastography. Techniques such as elastography and/or doppler imaging may be used via ultrasound to provide additional information such as higher density masses and visualizing fluid flow to help identify the proper duct to cannulate. Direct and/or indirect ultrasound and/or photoacoustic capabilities may be utilized. Intraoperative ultrasound and/or photoacoustic imaging may be used for image fusion.

Multimodal imaging may also include image fusion. For instance, input from an optical sensor and an ultrasonic transducer may be fused together to provide more relevant information for assisting with cannulation. In such instances, a picture of a direct visualization of the papilla with the ducts outlined on the wall of the duodenum may be provided, such as via user interface 120, which may provide an operator with a better idea of trajectory/approach.

Referring to environments 600A-600C, in embodiments, the target trajectory visualization 646-1 may illustrate a target angle of attack for respective devices (e.g., endoscopes, catheters, flexible elongate member 604-1) and the actual trajectory visualization 648-1 may illustrate a current angle for respective devices (e.g., endoscopes, catheters, flexible elongate members 604-1) based on actual positioning. In several such embodiments, an operator may align the actual trajectory visualization 648-1 with the target trajectory visualization 646-1 to properly position the flexible elongate member 604-1.

In several embodiments, controller 106 may display an image from a camera on the flexible elongate member 604-1, 604-2 (see FIGS. 6A-6B, 6D-6E), and detect and identify a papilla 642-1 for the medical professional. The controller 106 may determine a target trajectory 646-1 based on the image of the papilla 642-1, and overlay on the image to provide a visual cannulation path for a medical professional. In embodiments, an ultrasonic image may be obtained by an ultrasound sensor on the flexible elongate member 604-1, 604-2 to determine an image of the pancreatic and/or biliary ducts to generate a target trajectory 646-1. Once the papilla 642-1 and/or target trajectory 646-1 is identified, the controller 106 may determine a current trajectory of a tool extending from the flexible elongate member 604-1, 604-2, and overlay the trajectory 648-1. That is, the controller 106 may display images for the medical professional to better align the distal end of the flexible elongate member 604-1, such that the current trajectory and target trajectory 646-1, 648-1 are substantially aligned with each other on the image of the papilla 642-1 to improve cannulation and potentially reduce failed attempts. Alternatively, or additionally, the controller 106 may display images for the medical professional to better align the distal end of the flexible elongate member 604-2 with one of the biliary duct and the pancreatic duct to improve cannulation and potentially reduce failed attempts.

In embodiments, a laser, or light of a desired wavelength (e.g., from light source 634-1, 634-5) may be used to project a target angle of attack for the devices based on positioning (e.g., target trajectory visualization 646-1). In some embodiments, the laser/light (e.g., light source 634-1) may show the heading and/or direction for the tip of the flexible elongate member 604-1 (e.g., actual trajectory visualization 648-1). In embodiments, both the target trajectory 646-1 and the actual trajectory 648-1 are displayable on an image of the papilla 642-1, such that a medical professional can view and align the flexible elongate member in real-time. In some such embodiments, the heading and/or direction may inform an operator of the current trajectory of the distal end of the flexible elongate member as the flexible elongate member moves in the duodenum.

In many embodiments, the laser may be utilized to show an optimal approach angle, such as one set by the operator or automatically based on imaging input (e.g., from ultrasound integrated into the flexible elongate member 604-1) to then guide the movement towards and into a duct (e.g., biliary duct 626-1). The optimal approach angle may be shown as an extension of the duct anatomy, such as determined from ultrasound or photoacoustic imaging, to assist with proper alignment based on selected anatomy. In various embodiments, target trajectory visualization 646-1 and/or actual trajectory visualization 648-1 may be generated by software instead of a laser/light.

Referring to environments 600D-600F, in some embodiments, the pancreatic duct trajectory visualization 648-2 may include an entry point indication and/or outline of the pancreatic duct 628-2 and the biliary duct trajectory visualization 646-2 may include an entry point indication and/or outline of the biliary duct 626-2. In various embodiments, additional sensors, extended images, and/or trajectory visualization may assist with cannulation. In embodiments, one or more of light sources 634-2 may include a laser. In some embodiments, one or more of the trajectory visualizations 646-2, 648-2 may be generated by software instead of a light source.

Embodiments may include extended image overlay. For example, image of a scope or other ERCP instrument in a working channel may be virtually placed over an image presented via the user interface (e.g., an optical image). In such examples, this may assist with navigating to the biliary duct. In embodiments, information may be integrated from transducers to overlay on an image presented via the user interfaces. In such embodiments, appropriate transformations may be performed to enable visualization of optically invisible images (e.g., recolor, rescale, etc.). This information may provide accurate positional information and/or assist with navigation. In some embodiments, a ghost image of where a tool may be expected or desired to go may be generated.

In one or more embodiments, the trajectory may be fixed such that the initial trajectory shown stays constant, such as throughout a calibration procedure. In such embodiments, the trajectory may be fixed based on determination of an optimal angle into the duct. In embodiments, trajectory visualization may be adaptive such that sensors, imaging, and/or user input can be used to update the optimal trajectory for cannulation. For example, an operator may slowly move a catheter towards and into the duct based on the trajectory visualization. A measure and step approach may be used where, after small movements, sensors access the surroundings and adjust the trajectory if necessary and provide feedback. Feedback may be visual, showing an operator where/what to align with.

In some embodiments, feedback may be numerical and/or directional. In some such embodiments, appropriate movements to correct the value/feedback could be performed, such as automatically by controller 106. In various embodiments, trajectories may be used as supplemental information. In embodiments, feedback, such as visual, tactile, and/or audible, may be generated when a certain area or target tissue has been reached. In some embodiments, feedback, such as visual, tactile, and/or audible, may be generated when a certain area or target tissue has been reached In embodiments, the transducers may include and/or facilitate positional tracking/information, such as with ultrasound imaging and/or multimodal imaging to generate a three-dimensional map of selected anatomy based on one or more 2D images. In some embodiments, localization sensors may provide a third dimension for building a map of selected anatomy.

Figure 7A:
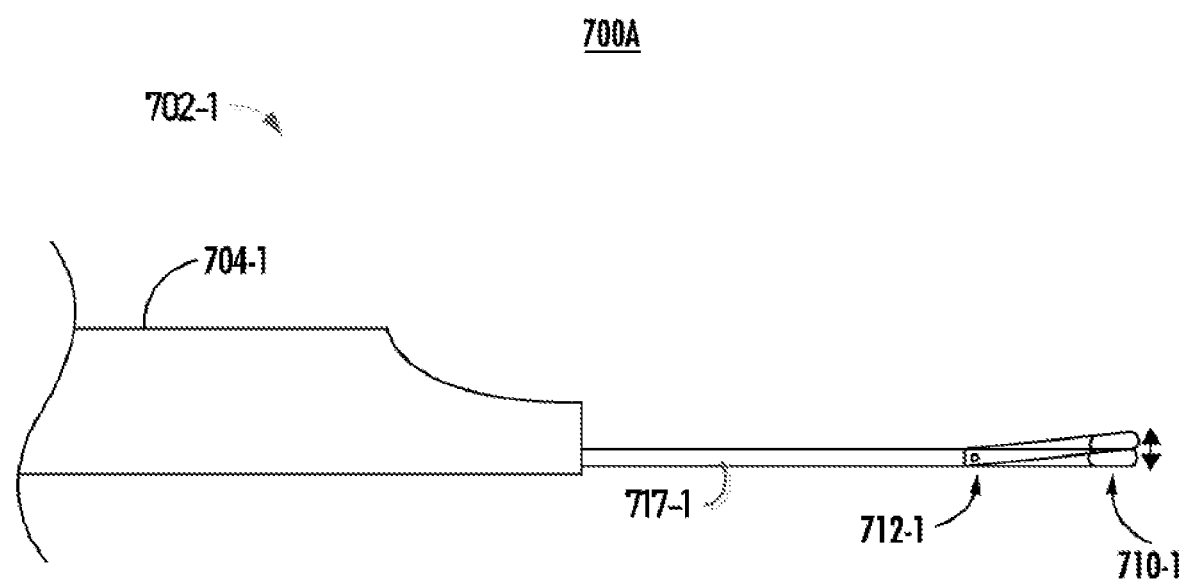
FIGS. 7A-7C illustrate various embodiments of a distal end of a flexible elongate member according to the present disclosure described herein.
Figure 7B:
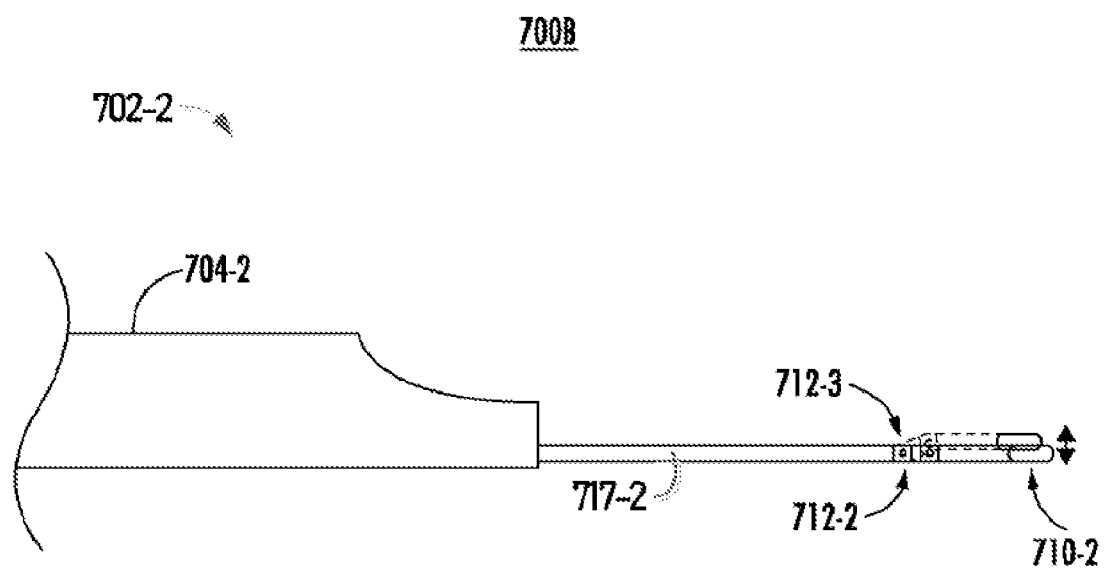
Figure 7C:
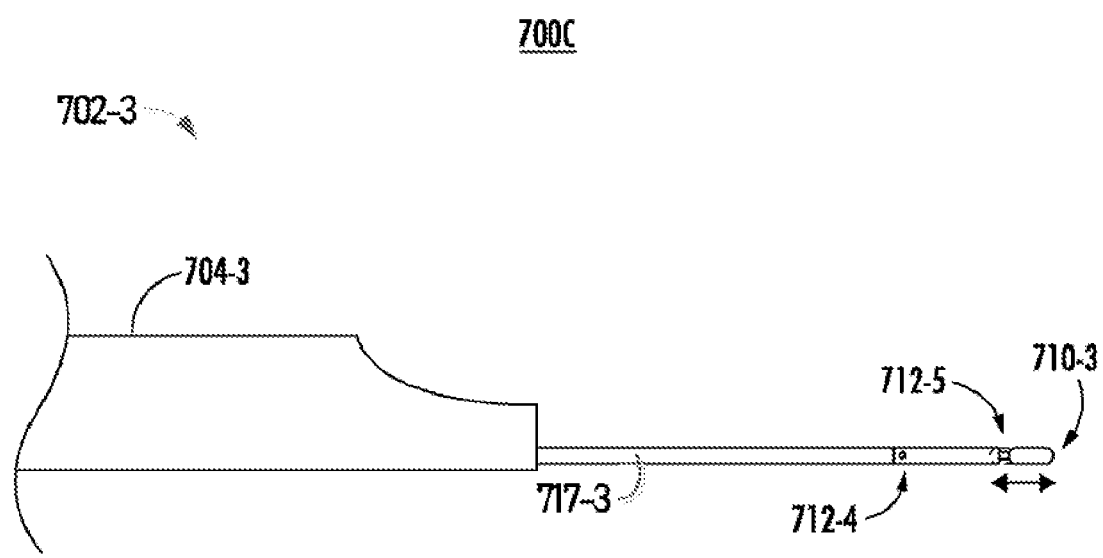

FIGS. 7A-7C illustrate various embodiments of flexible elongate members in environments 700A, 700B, 700C according to one or more embodiments described herein. In some embodiments, environments 700A, 700B, 700C may include one or more components that are the same or similar to one or more other components described herein. For example, flexible elongate member 704-1 may be the same or similar to one or more of flexible elongate members 104, 204, 304, 404, 504, 604-1, 604-2. Environment 700A includes a distal end of medical device 702-1 with flexible elongate member 704-1, articulation joint 712-1, transducer 710-1, and transducer member 717-1. Environment 700B includes medical device 702-2 with flexible elongate member 704-2, articulation joints 712-2, 712-3, transducer 710-2, and transducer member 717-2. Environment 700C includes medical device 702-3 with flexible elongate member 704-3, articulation joint 712-4, telescopic joint 712-5, transducer 710-1, and transducer member 717-3. In one or more embodiments described herein, mechanical vibration and/or movement may be utilized to assist in cannulation. In some embodiments, small movement/motion, such as forward and back or side-to-side may be used to assist with maneuvering, such as during a cannulation procedure. In some such embodiments, the small movements/motions may be automated. Embodiments are not limited in this context.

In environment 700A, articulation joint 712-1 may radially displace transducer 710-1 relative to at least a portion of medical device 702-1, such as a portion of transducer member 717-1. In environment 700B, articulation joints 712-2, 712-3 may radially displace transducer 710-2 about respective portions of medical device 702-2, such as respective portions of transducer member 717-2. In environment 700C, articulation joint 712-4 may radially displace transducer 710-3 relative to at least a portion of medical device 702-1, such as a portion of transducer member 717-3 and telescopic joint 712-5 may extend/retract transducer 710-3 longitudinally with respect to transducer member 717-3.

Figure 8:
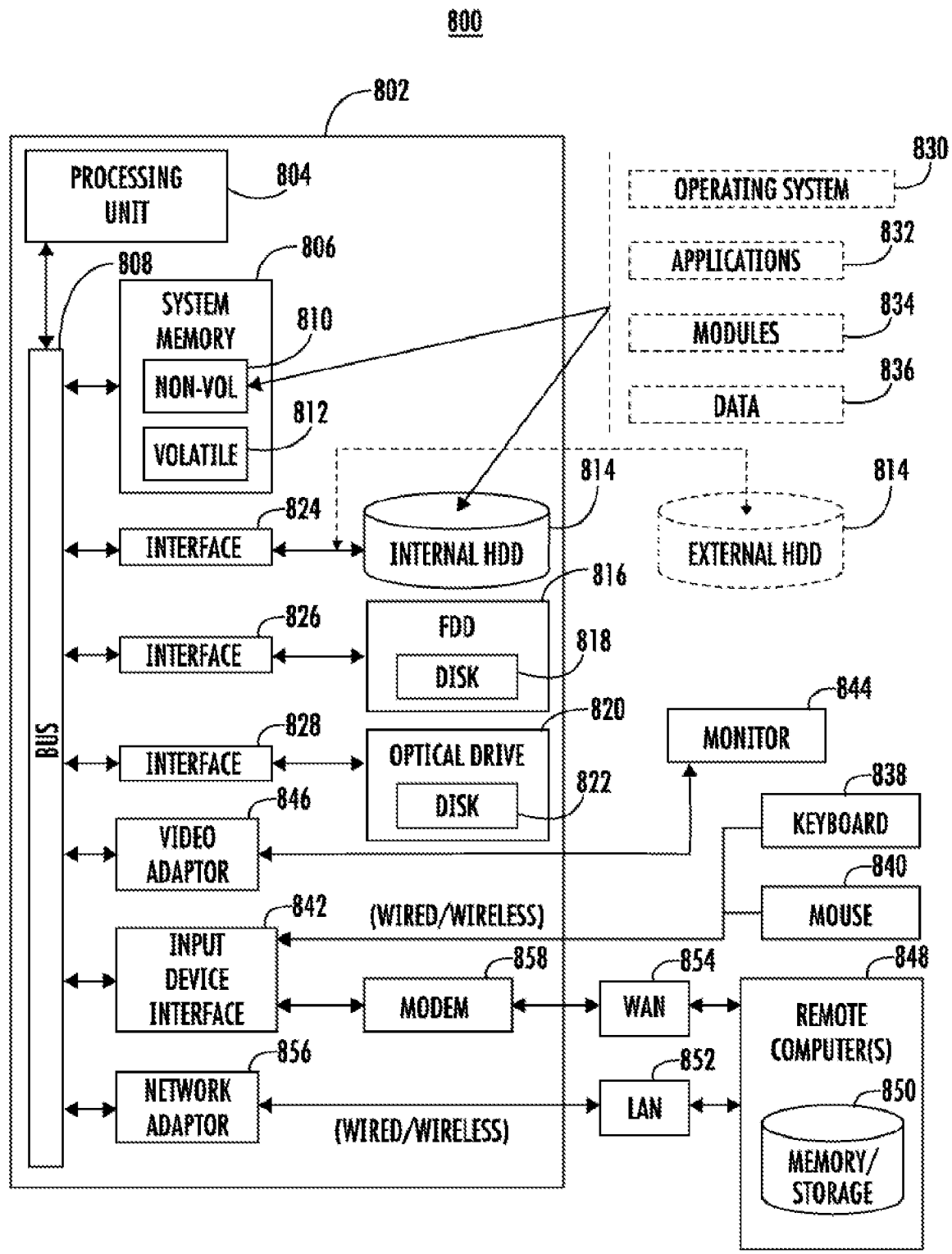
FIG. 8 illustrates an embodiment of a computing architecture according to the present disclosure described herein.

FIG. 8 illustrates an embodiment of a computing architecture 800 that may be suitable for implementing various embodiments as previously described. In various embodiments, the computing architecture 800 may comprise or be implemented as part of an electronic device and/or medical device. In some embodiments, the computing architecture 800 may be representative, for example, of one or more components described herein. In some embodiments, computing architecture 800 may be representative, for example, of a computing device that implements or utilizes one or more portions of components and/or techniques described herein, such as medical device 102, controller 106, one or more of transducer set 110, one or more of joint set 112, elongate member interface 114, processor 116, memory 118, and/or user interface 120. The embodiments are not limited in this context.

As used in this application, the terms "system" and "component" and "module" can refer to a computer-related entity, either hardware, a combination of hardware and software, software, or software in execution, examples of which are provided by the illustrative example of computing architecture 800 disclosed herein. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a controller 106 and the controller 106 can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Examples of connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806, and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. In some embodiments, system memory 806 may include main memory. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by an HDD interface 824, an FDD interface 826 and an optical drive interface 828, respectively. The HDD interface 824 for external drive implementations can include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include or implement, for example, the various techniques, applications, and/or components described herein.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808 but can be connected by other interfaces such as a parallel port, IEEE 994 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. In various embodiments, one or more interactions described herein may occur via the networked environment. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854 or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are illustrative examples and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operation in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

What is claimed is:

1. An apparatus comprising:
   a processor;
   a first transducer;
   a second transducer positioned distal to the first transducer; and
   a memory comprising instructions that, when executed by the processor, cause the processor to:
   position the second transducer within at least a portion of a focal region of the first transducer,
   generate a first image with the first transducer, the first image configured to include a characteristic of a wall of a body lumen, the wall of the body lumen comprising a duodenal wall,
   generate a second image with the second transducer, the second image configured to include a characteristic beyond the wall of the body lumen that comprises a duct beyond an entry point in the wall of the body lumen, the duct selected from a bile duct and a pancreatic duct,
   create a combined image comprising the characteristic of the wall of the body lumen and the characteristic beyond the wall of the body lumen based on the first image and the second image, and
   determine a trajectory visualization based on the first and second images, the trajectory visualization selected from a biliary duct trajectory visualization and a pancreatic duct trajectory visualization;
   the first transducer comprising an optical sensor, the first image comprising an optical image, the second transducer comprising an ultrasonic transducer, and the second image comprising an ultrasound image.

2. The apparatus of claim 1, wherein the memory comprises instructions to determine a target trajectory visualization and an actual trajectory visualization.

3. The apparatus of claim 1, wherein the memory comprises instructions to generate an indication of the trajectory visualization in the combined image.

4. The apparatus of claim 1, wherein the memory comprises instructions to generate an indication of the trajectory visualization with a light source configured to be inside the body lumen.

5. The apparatus of claim 1, wherein the memory comprises instructions configured to contact the wall of the body lumen with the second transducer to facilitate the generation of the second image.

6. The apparatus of claim 1, wherein the apparatus is configured to maintain the first transducer at a distance from the wall of the body lumen when generating the first image, and wherein the apparatus is configured to place the second transducer in contact with the wall of the body lumen when generating the second image.

7. A method comprising:
   generating a first image with a first transducer that is maintained at a distance from a wall of a body lumen, the first image to include a characteristic of the wall of the body lumen, the wall of the body lumen comprising a duodenal wall;
   generating a second image with a second transducer that is placed in contact with the wall of the body lumen, the second transducer positioned distal to the first transducer and within at least a portion of a focal region of the first transducer, the second image to include a characteristic beyond the wall of the body lumen, the characteristic beyond the wall of the body lumen comprising a structure behind the duodenal wall selected from a bile duct and a pancreatic duct; and
   creating a combined image comprising the characteristic of the wall of the body lumen and the characteristic beyond the wall of the body lumen based on the first image and the second image; and
   determining a trajectory visualization based on the first and second images, the trajectory visualization selected from a biliary duct trajectory visualization and a pancreatic duct trajectory visualization;
   the first transducer comprising an optical sensor, the first image comprising an optical image, the second transducer comprising an ultrasonic transducer, and the second image comprising an ultrasound image.

8. The method of claim 7, further comprising determining a target trajectory visualization and an actual trajectory visualization and aligning the actual trajectory visualization with the target trajectory visualization.

9. The method of claim 7, further comprising generating an indication of the trajectory visualization in the combined image.

10. The method of claim 7, further comprising generating an indication of the trajectory visualization with a light source inside the body lumen.

11. The method of claim 7, further comprising contacting the wall of the body lumen with the second transducer to facilitate the generation of the second image.

12. The method of claim 7, further comprising inflating one or more balloons to position the first transducer or the second transducer within the body lumen.

* * * * *